(12) United States Patent
Cho et al.

(10) Patent No.: US 6,358,703 B1
(45) Date of Patent: Mar. 19, 2002

(54) EXPRESSION SYSTEM FOR FACTOR VIII

(75) Inventors: Myung-Sam Cho, Pinole; Sham-Yuen Chan, El Sobrante; William Kelsey, Alameda; Helena Yee, San Francisco, all of CA (US)

(73) Assignee: Bayer Corporation, Berkeley, CA (US)

( * ) Notice: Subject to any disclaimer, the term of this patent is extended or adjusted under 35 U.S.C. 154(b) by 0 days.

(21) Appl. No.: 09/209,916

(22) Filed: Dec. 10, 1998

(51) Int. Cl.$^7$ ................................................. C12P 21/06
(52) U.S. Cl. ...................... 435/69.1; 435/69.6; 435/325; 435/346; 435/366; 435/372; 530/350; 530/383
(58) Field of Search ............................... 435/69.1, 69.6, 435/325, 346, 366, 372, 404; 530/350, 383

(56) References Cited

U.S. PATENT DOCUMENTS 5,612,213 A * 3/1997 Chan .............................. 435/6
5,804,420 A * 9/1998 Chan et al. ................. 435/69.6

FOREIGN PATENT DOCUMENTS

EP 0 254 076 * 1/1988
SE WO 91/09122 * 6/1991

OTHER PUBLICATIONS

Pu et al. Rapid Establishment of High–Producing Cell Lines Using Dicistronic Vectors with Glutamine Synthetase as teh Selection Marker. Mol. Biotechnol. 10: 17–25, 1998.*
Kane, S.E. Selection of Transfected Cells and Coamplification of Transfected Genes. Methods Mol. Biol. 62: 359–367, 1997.*
Bebbington et al. High–Level Expression of a Recombinant Antibody from Myeloma Cells using a Glutamine Synthetase Gene as an Amplifiable Selectable Marker. Bio/Technol. 10: 169–175, Feb. 1992.*

* cited by examiner

Primary Examiner—Karen Cochrane Carlson
Assistant Examiner—Hope A. Robinson
(74) Attorney, Agent, or Firm—Melissa A. Shaw; John W. Mahoney

(57) ABSTRACT

This invention describes a protein-free production process for proteins having factor VIII procoagulant activity. The process includes the derivation of stable human cell clones with high productivity for B-domain deleted Factor VIII, and (2) the adaptation of cells to grow in a medium free of plasma-derived proteins.

8 Claims, 5 Drawing Sheets

```
   1  ATRRYYLGAV  ELSWDYMQSD  LGELPVDARF  PPRVPKSFPF  NTSVVYKKTL
  51  FVEFTVHLFN  IAKPRPPWMG  LLGPTIQAEV  YDTVVITLKN  MASHPVSLHA
 101  VGVSYWKASE  GAEYDDQTSQ  REKEDDKVFP  GGSHTYVWQV  LKENGPMASD
 151  PLCLTYSYLS  HVDLVKDLNS  GLIGALLVCR  EGSLAKEKTQ  TLHKFILLFA
 201  VFDEGKSWHS  ETKNSLMQDR  DAASARAWPK  MHTVNGYVNR  SLPGLIGCHR
 251  KSVYWHVIGM  GTTPEVHSIF  LEGHTFLVRN  HRQASLEISP  ITFLTAQTLL
 301  MDLGQFLLFC  HISSHQHDGM  EAYVKVDSCP  EEPQLRMKNN  EEAEDYDDDL
 351  TDSEMDVVRF  DDDNSPSFIQ  IRSVAKKHPK  TWVHYIAAEE  EDWDYAPLVL
 401  APDDRSYKSQ  YLNNGPQRIG  RKYKKVRFMA  YTDETFKTRE  AIQHESGILG
 451  PLLYGEVGDT  LLIIFKNQAS  RPYNIYPHGI  TDVRPLYSRR  LPKGVKHLKD
 501  FPILPGEIFK  YKWTVTVEDG  PTKSDPRCLT  RYYSSFVNME  RDLASGLIGP
 551  LLICYKESVD  QRGNQIMSDK  RNVILFSVFD  ENRSWYLTEN  IQRFLPNPAG
 601  VQLEDPEFQA  SNIMHSINGY  VFDSLQLSVC  LHEVAYWYIL  SIGAQTDFLS
 651  VFFSGYTFKH  KMVYEDTLTL  FPFSGETVFM  SMENPGLWIL  GCHNSDFRNR
 701  GMTALLKVSS  CDKNTGDYYE  DSYEDISAYL  LSKNNAIEPR  SFSQNPPVLK
 751  RHQREITRTT  LQSDQEEIDY  DDTISVEMKK  EDFDIYDEDE  NQSPRSFQKK
 801  TRHYFIAAVE  RLWDYGMSSS  PHVLRNRAQS  GSVPQFKKVV  FQEFTDGSFT
 851  QPLYRGELNE  HLGLLGPYIR  AEVEDNIMVT  FRNQASRPYS  FYSSLISYEE
 901  DQRQGAEPRK  NFVKPNETKT  YFWKVQHHMA  PTKDEFDCKA  WAYFSDVDLE
 951  KDVHSGLIGP  LLVCHTNTLN  PAHGRQVTVQ  EFALFFTIFD  ETKSWYFTEN
1001  MERNCRAPCN  IQMEDPTFKE  NYRFHAINGY  IMDTLPGLVM  AQDQRIRWYL
1051  LSMGSNENIH  SIHFSGHVFT  VRKKEEYKMA  LYNLYPGVFE  TVEMLPSKAG
1101  IWRVECLIGE  HLHAGMSTLF  LVYSNKCQTP  LGMASGHIRD  FQITASGQYG
1151  QWAPKLARLH  YSGSINAWST  KEPFSWIKVD  LLAPMIIHGI  KTQGARQKFS
1201  SLYISQFIIM  YSLDGKKWQT  YRGNSTGTLM  VFFGNVDSSG  IKHNIFNPPI
1251  IARYIRLHPT  HYSIRSTLRM  ELMGCDLNSC  SMPLGMESKA  ISDAQITASS
1301  YFTNMFATWS  PSKARLHLQG  RSNAWRPQVN  NPKEWLQVDF  QKTMKVTGVT
1351  TQGVKSLLTS  MYVKEFLISS  SQDGHQWTLF  FQNGKVKVFQ  GNQDSFTPVV
1401  NSLDPPLLTR  YLRIHPQSWV  HQIALRMEVL  GCEAQDLY
```

Fig. 1

```
GGCAATGGAG CGTGAAGAAG GGCCCCAGGG CTGACCCCGG CAAACGTGAC   (50)
CCGGGGCTCC GGGGTGACCC AGGCAAGCGT GGCCAAGGGG CCCGTGGGTG  (100)
ACACAGGCAA CCCTGACAAA GGCCCCCCAG GAAAGACCCC CGGGGGGCAT  (150)
CGGGGGGGTG TTGGCGGGTC ATGGGGGGGG CGGGTCATGC CGCGCATTCC  (200)
TGGAAAAAGT GGAGGGGGCG TGGCCTTCCC CCCGCGGCCC CCTAGCCCCC  (250)
CCGCAGAGAG CGGCGCAACG GCGGGCGAGC GGCGGGGGGT CGGGGTCCGC  (300)
GGGCTCCGGG GGCTGCGGGC GGTGGATGGC GGCTGGCGTT CCGGGGATCG  (350)
GGGGGGGGTC GGGGGGCGCT GCGCGGGCGC AGCCATGCGT GACCGTGATG  (400)
AG                                                     (402)
```

Fig._2

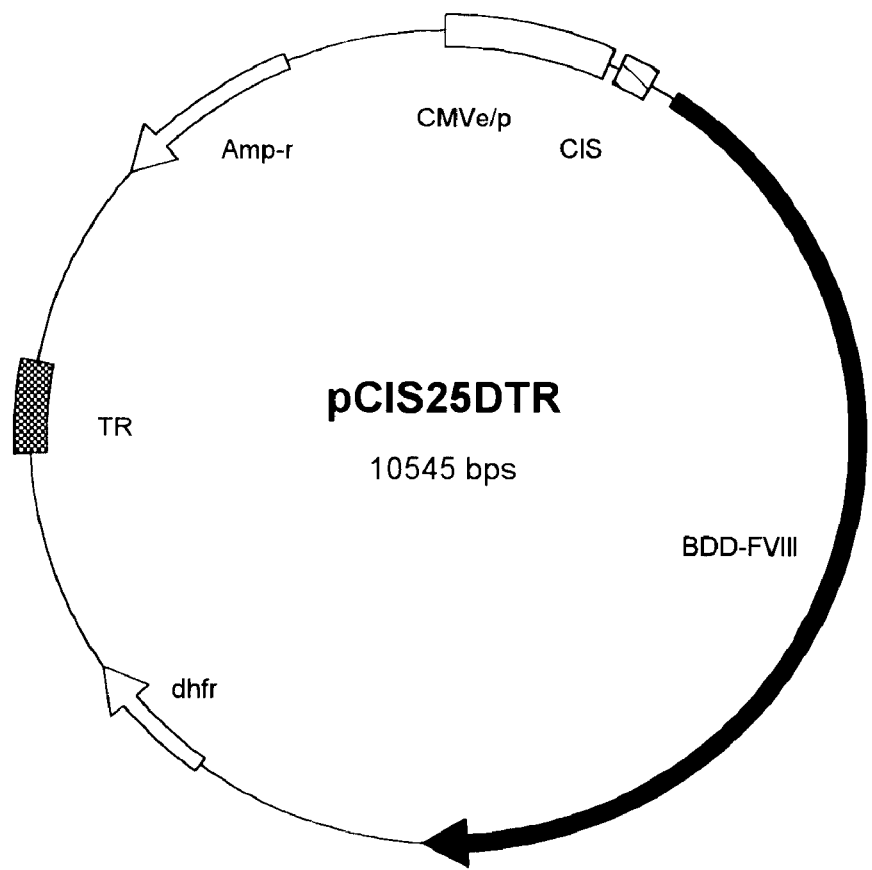
Fig._3

Fig._4A
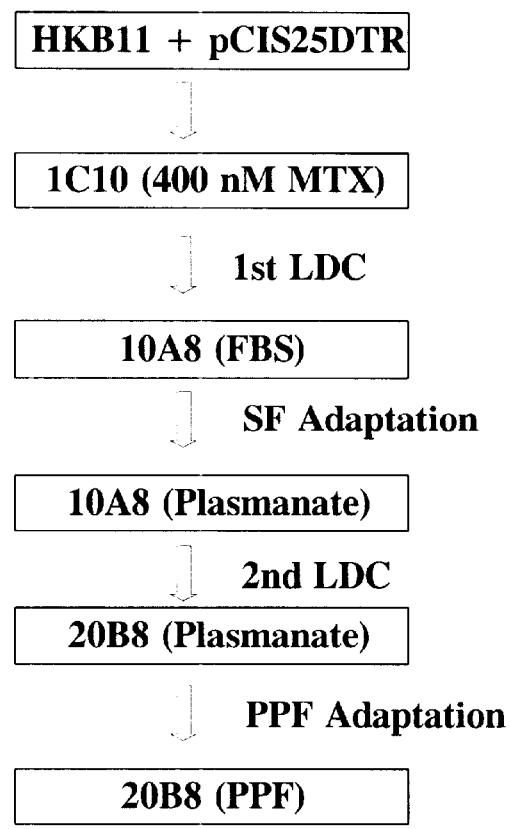
Fig._4B
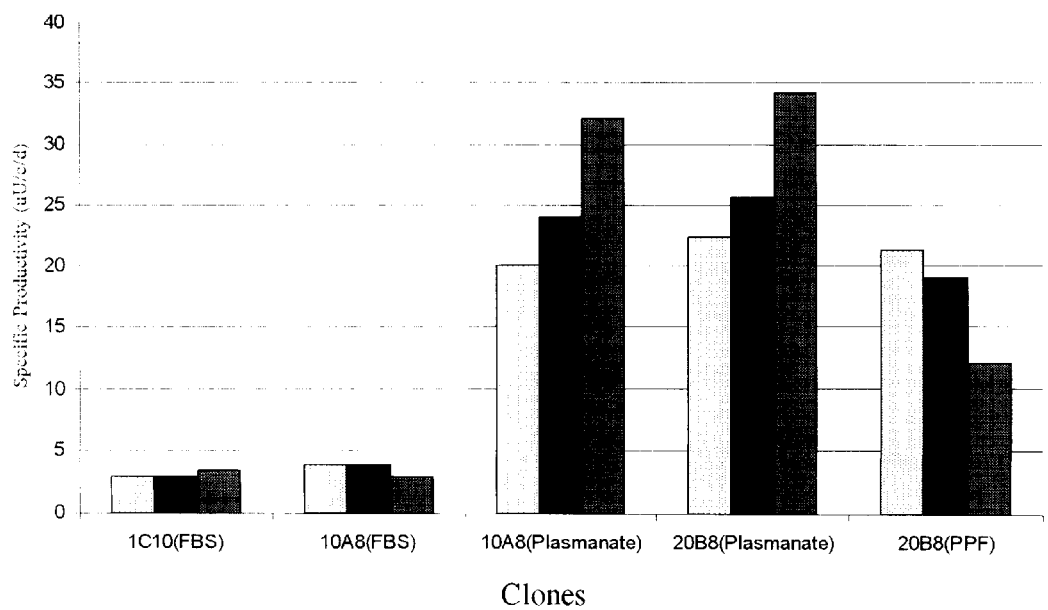

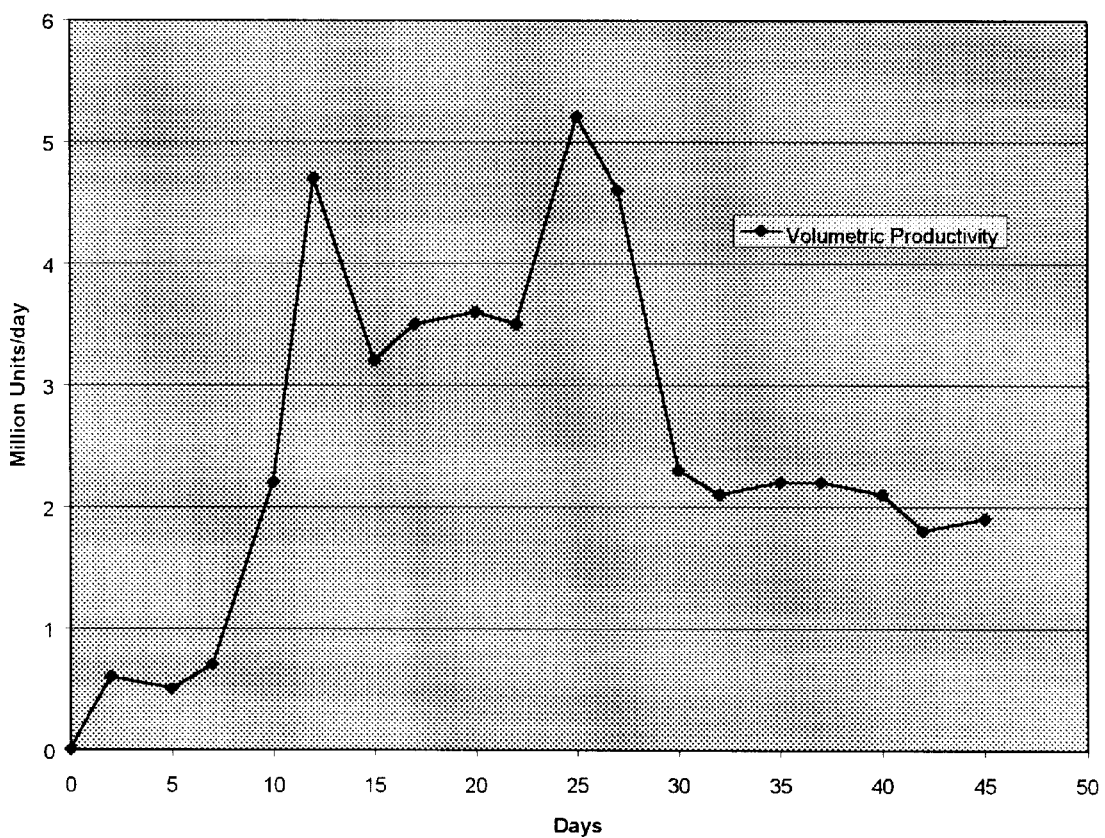
Fig._5

EXPRESSION SYSTEM FOR FACTOR VIII

RELATED APPLICATIONS

The application to Cho designated Ser. No. 09/209,920, filed Dec. 10, 1998, now U.S. Pat. No. 6,136,599, title "Human hybrid host cell for mammalian gene expression," and the application to Cho and Chan designated Ser. No. 09/209915, filed Dec. 10, 1998, now U.S. Pat. No. 6,180,108, titled "Terminal repeat sequence of Epstein-Barr virus enhances drug selection ratio," contain related subject matter.

BACKGROUND OF THE INVENTION

1. Field

The present invention relates to an improved production method for factor VIII and its derivatives. The method relates generally to vector construction, transfection, and selection of cell lines with enhanced productivity under protein-free conditions. In particular, this invention relates to a process for preparing a protein with factor VIII procoagulant activity on an industrial scale.

2. Background

Human factor VIII is a trace plasma glycoprotein involved as a cofactor in the activation of factor X and factor IXa. Inherited deficiency of factor VIII results in the X-linked bleeding disorder hemophilia A which can be treated successfully with purified factor VIII. The replacement therapy of hemophilia A has evolved from the use of plasma-derived factor VIII to the use of recombinant factor VIII obtained by cloning and expressing the factor VIII cDNA in mammalian cells. (Wood et al., 1984, Nature 312: 330).

Factor VIII has a domain organization of A1-A2-B-A3-C1-C2 and is synthesized as a single chain polypeptide of 2351 amino acids, from which a 19-amino acid signal peptide is cleaved upon translocation into the lumen of the endoplasmic reticulum. Due to the fact that factor VIII is heavily glycosylated, high-level expression (>0.2 pg/c/d) of factor VIII has been difficult to achieve (Lind et al., 1995, Eur J Biochem. 232: 19–27; Kaufman et al., 1989, Mol Cell Biol. 9: 1233–1242). Expression of factor VIII in mammalian cells is typically 2–3 orders of magnitude lower than that observed with other genes using similar vectors and approaches. The productivity of production cell lines for factor VIII has been in the range of 0.5–1 $\mu$U/c/d (0.1–0.2 pg/c/d).

It has been demonstrated that the B-domain of factor VIII is dispensable for procoagulant activity. Using truncated variants of factor VIII, improved expression of factor VIII in mammalian cells has been reported by various groups (Lind et al., 1995, Eur J Biochem 232: 19–27; Tajima et al., 1990, Proc $6^{th}$ Int Symp H.T. p.51–63; U.S. Pat. No. 5,661,008 to Almstedt, 1997). However, the expression level of the factor VIII variants remained below 1 pg/c/d from a stable cell clone.

SUMMARY OF THE INVENTION

We have now discovered (i) a method which derives cell lines with extremely high productivity of proteins having factor VIII procoagulant activity, and (ii) a plasma protein-free production process for proteins having factor VIII procoagulant activity.

A process for the production of proteins having factor VIII procoagulant activity at the industrial scale is disclosed. Using a newly created cell host, cell clones with specific productivities in the range of 2–4 pg/cell/day (10–20 $\mu$U/c/d) were derived. Under serum-free conditions, one clone has sustained a daily productivity of 2–4 pg/c/d. Clones with this high level of productivity are able to produce 3–4 million units per day in a 15-liter perfusion fermenter. One unit of factor VIII activity is by definition the activity present in one milliliter of plasma. One pg of factor VIII is generally equivalent to about 5 $\mu$U of FVIII activity.

As used herein, a protein having factor VIII procoagulant activity is a protein which causes the activation of Factor X in an in vitro or in vivo model system. As non-limiting examples, this definition includes full length recombinant human factor VIII and the B domain deleted factor VIII whose sequence is described in FIG. 1.

A high level of expression of a protein having factor VIII procoagulant activity means at least about 2 $\mu$U/c/d, or more preferably at least about 4 $\mu$U/c/d, or most preferably at least about 5 $\mu$U/c/d, of factor VIII activity if grown in plasma derived protein-free medium, or at least about 4 $\mu$U/c/d, or more preferably at least about 8 $\mu$U/c/d, or most preferably at least about 10 $\mu$U/c/d, of factor VIII activity if grown in medium supplemented with plasma derived protein. When the protein expressed is BDD-FVIII, cell lines having specific productivities up to about 15 $\mu$U/c/d, more preferably up to about 20 $\mu$U/c/d may be obtained by the method described herein.

As used herein to describe the origin of cell lines, "derived from" is intended to include, but not be limited to, normal mitotic cell division and processes such as transfections, cell fusions, or other genetic engineering techniques used to alter cells or produce cells with new properties.

BRIEF DESCRIPTION OF THE FIGURES

FIG. 1. Amino Acid Sequence of BDD-FVIII (SEQ ID NO:1).

FIG. 2. Sequence of terminal repeat (TR) sequence isolated from Epstein-Barr virus (SEQ ID NO:2).

FIG. 3. Plasmid map of pCIS25DTR.

FIG. 4(a). Derivation of clone 20B8.

FIG. 4(b). Comparison of productivities of several clones in various media. Three data points are presented from a two month stability test of each clone.

FIG. 5. Volumetric productivity of clone 20B8.

SPECIFIC EMBODIMENTS

FVIII Assay

The activity of factor VIII derivatives obtained from recombinant gene expression in methotrexate (MTX)-resistant cell populations was measured by a chromogenic assay. Activity was quantitated using Coatest® factor VIII:C/4 kit (Cromogenix, Molndal, Sweden) according to manufacturer's instructions. A U.S. standard antihemophilic factor (factor VIII) known as MEGA 1 (Office of Biologics Research and Review, Bethesda, Md.) was used as the standard of measurement in this assay. See Barrowcliffe, 1993, Thromb Haem 70: 876.

Construction of Expression Vectors for B-domain Deleted FVIII

The sequence of the B-domain deleted (BDD) FVIII is shown in FIG. 1. The 90-kD and 80-kD chains were linked by a linker consisting of 14 amino acids. See Chan, S.-Y., "Production of Recombinant Factor VIII in the Presence of Liposome-like Substances of Mixed Composition," U.S. patent application Ser. No. 08/634,001, filed Apr. 16, 1996.

The expression vector for BDD-FVIII was made using standard recombinant DNA techniques. The structure of the expression vector (pCIS25DTR) is shown in FIG. 3. The vector includes a transcriptional unit for BDD-FVIII and a selectable marker, dihydrofolate reductase (dhfr). In addition a terminal repeat sequence from Epstein-Barr virus, which shows enhanced drug selection ratio, (FIG. 2) was inserted into the vector to increase the integration efficiency. The vector is essentially a construct of a vector (deposited ATCC 98879) which has been engineered to include a transcriptional unit corresponding to the sequence shown in FIG. 1. Further information about the terminal repeat sequence can be found in the related patent application, incorporated herein by reference, to Cho and Chan Ser. No. 09/209,915, "Terminal repeat sequence of Epstein-Barr virus enhances drug selection ratio," filed on the same day as the current application.

Similar vectors can be constructed and used by those having skill in the art to obtain cells expressing proteins having factor VIII procoagulant activity. For example, coding sequences coding for known variants of factor VIII which retain procoagulant activity can be substituted for the BDD-FVIII coding sequence. Also, instead of dhfr, other selectable markers can be used, such as glutamine synthetase (gs) or multidrug-resistance gene (mdr). The choice of a selection agent must be made accordingly, as is known in the art, i.e. for dhfr, the preferred slection agent is methotrexate, for gs the preferred selection agent is methionine sulfoximine, and for mdr the preferred selection agent is colchicine.

WORKING EXAMPLES
Derivation of Cell Lines Expressing BDD-FVIII: Transfection, Drug Selection and Gene Amplification Thirty micrograms of pCIS25DTR DNA was transferred into HKB11 (ATCC deposit no. CRL 12568—a hybrid of 293S cells and human Burkitt's lymphoma cells, see U.S. patent application to Cho et al. filed on the same day as the current application Ser. No. 09/209,920, incorporated herein by reference) cells by electroporation set at 300 volts and 300 micro farads (BTX Electro cell Manipulator 600) using a 2 mm cuvette (BTX part #620). In comparative experiments done to parallel work with the HKB11 cells, CHO (Chinese hamster ovary) and 293S (human embryonic kidney) cells were transfected using a cationic lipid reagent DMRIE-C (Life Technologies, Gaithersburg, Md.) according to a protocol provided by the Life Technologies. Amplification of transfected cells was done with increasing methotrexate (MTX) concentrations (100 nM, 200 nM, 400 nM, and 800 nM) at $1 \times 10^6$ cells per 96 well plate in a MTX-selection medium lacking hypoxanthine and thymidine (DME/F12 media without hypoxanthine and thymidine plus 5% dialyzed fetal bovine serum from Hyclone, Logan, Utah). MTX resistant cells were scored for growth, and secretion of the BDD-FVIII was screened using a Coatest® factor VIII kit about 2–3 weeks post-transfection. The cultivation of cells were done at 37° C. in a humidified 5% $CO_2$ incubator.

Limiting Dilution Cloning

Single cell clones (SCC) were derived by limiting dilution cloning (LDC) of high producing populations in 96 well plates under serum-free conditions. Cells were seeded at 1–10 cells per well in DME/F12 media supplemented with Humulin® recombinant insulin (Lilly, Indianapolis, Ind.) at 10 μg/ml, 10X essential amino acids (Life Technology, Gaithersburg, Md.), and Plasmanate® human plasma protein fraction (Bayer, Clayton, N.C.). Plasmanate® human plasma protein (HPP) fraction contains human albumin (88%) and various globulins (12%). The clones were screened for BDD-FVIII productivity using the Coatest® factor VIII kits. The highest producing clones were selected for stability evaluation in shake flasks. For HKB cells, the first round LDC was performed using selection medium supplemented with 5% dialyzed FBS. The second round LDC was done in serum-free but Plasmanate® HPP fraction-containing medium using the first SCC adapted in serum-free medium supplemented with Plasmanate® HPP fraction.

Derivation of HKB Clone 20B8

As summarized in FIG. 4(a), the initial population 1C10 was derived from the HKB cells transfected with pCIS25DTR after amplification with 400 nM MTX in the selection medium with 5% FBS. One of the first single cell clones (SCCs), 10A8, derived from 1C10 by a LDC using a selection medium supplemented with 5% FBS was adapted in serum-free medium supplemented with Plasmanate® HPP fraction. Unexpectedly, 10A8 showed extremely increased levels of rFVIII production at this stage (FIG. 4b). Therefore, we did a second LDC using the medium supplemented with Plasmanate® HPP fraction. The productivity of SCCs (e.g. 20B8) derived from the second LDC was similar with Plasmanate® HPP fraction-adapted 10A8. 20B8 showed higher levels of BDD-FVIII than original 10A8 derived from the first LDC in serum-containing medium. Finally, 20B8 was adapted to growth in plasma protein-free (PPF) medium. Samples of 20B8 were deposited at the American Type Culture Collection (Manassas, Va.) (ATCC deposit no. CRL-1 2582).

As shown in Table 1, HKB clones exhibit superior productivity for BDD-FVIII. A 10–20 fold increase in productivity was observed in HKB cells when compared to clones derived from transfected CHO and 293S cells. HKB cells, which do not form large aggregates of cells when grown in suspension culture, are preferred cells for the expression of proteins having factor VIII procoagulant activity.

TABLE 1

Expression of FVIII and BDD-FVIII in human and rodent cell lines

| FVIII Derivatives | Specific Productivity ($\mu$U/c/d)* | | | |
|---|---|---|---|---|
| | BHK | 293s | CHO | HKB |
| Full length FVIII | 0.45 | 1.2 | 0.5 | 1.0 |
| BDD-FVIII | ND | 2.5 | 1.0 | 20 |

*Average of 5 high producing clones (in serum-free media)
ND = Not done

Plasma-Protein-free Adaptation of Clones

HKB clones that have been adapted to grow as serum-free suspension cultures were further weaned of plasma protein supplements. The weaning was done in sterile polycarbonate shake flasks (Corning, Corning, N.Y.) at a cell density of about $0.5 \times 10^6$ cells/ml using plasma derived protein free medium. The plasma protein free (PPF) medium was DME/F12 medium supplemented with pluronic F68 (0.1%), $CuSO_4$ (50 nM), and $FeSO_4$/EDTA (50 μM). Complete medium exchange was done every 48 hours and the shake flasks were re-seeded at $0.5 \times 10^6$ cells/ml.

Fermentation of Clone 20B8

The productivity of clone 20B8 was evaluated in a 15-liter perfusion fermenter. The fermenter was seeded with clone 20B8 cells at a density of about $3 \times 10^6$ cells/ml. The fermenter was perfused at a rate of 4 volumes per day with the serum-free production medium as described in the preceding paragraph. A final cell density of $2 \times 10^7$ cells/ml was sustained throughout the evaluation period (45 days). As shown in FIG. 5, during the first 4 weeks of fermentation, clone 20B8 was perfused with the serumfree production medium supplemented with Plasmanate® HPP fraction and was able to sustain high productivity. From day 28 to the end of the fermentation run, the cells were perfused with the same serumfree production medium but without Plasmanate® HPP fraction. As shown in FIG. 5, the cells continued to produce high levels of FVIII in a plasma derived protein-free environment. "Plasma derived protein-free" means that essentially no proteins isolated from plasma have been added to the medium.

DISCUSSION

The derivation of HKB cells provides a protein-free production system to produce not only BDD-FVIII but other therapeutic proteins as well. Proteins produced from HKB cells have human glycosylation patterns which may improve the half-life of certain glycoproteins in vivo. These cells should also be useful for the production of adenovirus and adeno-associated virus strains that have been designed for gene therapy purposes.

The above examples are intended to illustrate the invention and it is thought variations will occur to those skilled in the art. Accordingly, it is intended that the scope of the invention should be limited only by the claims below.

We claim:

1. A method of producing and isolating a protein having factor VIII activity comprising growing cells designated by the American Type Culture Collection as CRL-12568 which include a sequence coding for the protein operably linked to a promoter, the growing being under conditions sufficient to express the protein and isolating the protein.

2. The method of claim 1 wherein the protein has the amino acid sequence designated as SEQ ID NO:1.

3. The method of claim 1 wherein the protein is expressed at a level of at least 2 $\mu$U/c/d when the cells are grown in a plasma derived protein-free medium.

4. The method of claim 3 wherein the protein is expressed at a level of at least 4 $\mu$U/c/d.

5. The method of claim 4 wherein the protein is expressed at a level of at least 5 $\mu$U/c/d.

6. A human cell line obtained from cells designated by the American Type Culture Collection as CRL-12568 which express a protein having factor VIII activity.

7. The human cell line of claim 6 which expresses B-domain deleted factor VIII.

8. A cell line designated by the American Type Culture Collection as CRL-12582.

* * * * *

SEQUENCE LISTING

```
<160> NUMBER OF SEQ ID NOS: 2

<210> SEQ ID NO 1
<211> LENGTH: 1438
<212> TYPE: PRT
<213> ORGANISM: Artificial Sequence
<220> FEATURE:
<223> OTHER INFORMATION: Description of Artificial Sequence:  Derived
      from human factor VIII sequence

<400> SEQUENCE: 1

Ala Thr Arg Arg Tyr Tyr Leu Gly Ala Val Glu Leu Ser Trp Asp Tyr
  1               5                  10                  15

Met Gln Ser Asp Leu Gly Glu Leu Pro Val Asp Ala Arg Phe Pro Pro
                 20                  25                  30

Arg Val Pro Lys Ser Phe Pro Phe Asn Thr Ser Val Val Tyr Lys Lys
             35                  40                  45

Thr Leu Phe Val Glu Phe Thr Val His Leu Phe Asn Ile Ala Lys Pro
         50                  55                  60

Arg Pro Pro Trp Met Gly Leu Leu Gly Pro Thr Ile Gln Ala Glu Val
     65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255
```

-continued

```
Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
            290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
            370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
```

-continued

```
            675                 680                 685
Ile Leu Gly Cys His Asn Ser Asp Phe Arg Asn Arg Gly Met Thr Ala
        690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Pro Val Leu Lys Arg His
        740                 745                 750
Gln Arg Glu Ile Thr Arg Thr Leu Gln Ser Asp Gln Glu Ile
        755                 760                 765
Asp Tyr Asp Asp Thr Ile Ser Val Glu Met Lys Lys Glu Asp Phe Asp
770                 775                 780
Ile Tyr Asp Glu Asp Glu Asn Gln Ser Pro Arg Ser Phe Gln Lys Lys
785                 790                 795                 800
Thr Arg His Tyr Phe Ile Ala Ala Val Glu Arg Leu Trp Asp Tyr Gly
                805                 810                 815
Met Ser Ser Ser Pro His Val Leu Arg Asn Arg Ala Gln Ser Gly Ser
                820                 825                 830
Val Pro Gln Phe Lys Lys Val Val Phe Gln Glu Phe Thr Asp Gly Ser
                835                 840                 845
Phe Thr Gln Pro Leu Tyr Arg Gly Glu Leu Asn Glu His Leu Gly Leu
850                 855                 860
Leu Gly Pro Tyr Ile Arg Ala Glu Val Glu Asp Asn Ile Met Val Thr
865                 870                 875                 880
Phe Arg Asn Gln Ala Ser Arg Pro Tyr Ser Phe Tyr Ser Ser Leu Ile
                885                 890                 895
Ser Tyr Glu Glu Asp Gln Arg Gln Gly Ala Glu Pro Arg Lys Asn Phe
                900                 905                 910
Val Lys Pro Asn Glu Thr Lys Thr Tyr Phe Trp Lys Val Gln His His
                915                 920                 925
Met Ala Pro Thr Lys Asp Glu Phe Asp Cys Lys Ala Trp Ala Tyr Phe
        930                 935                 940
Ser Asp Val Asp Leu Glu Lys Asp Val His Ser Gly Leu Ile Gly Pro
945                 950                 955                 960
Leu Leu Val Cys His Thr Asn Thr Leu Asn Pro Ala His Gly Arg Gln
                965                 970                 975
Val Thr Val Gln Glu Phe Ala Leu Phe Phe Thr Ile Phe Asp Glu Thr
                980                 985                 990
Lys Ser Trp Tyr Phe Thr Glu Asn Met Glu Arg Asn Cys Arg Ala Pro
        995                 1000                1005
Cys Asn Ile Gln Met Glu Asp Pro Thr Phe Lys Glu Asn Tyr Arg Phe
    1010                1015                1020
His Ala Ile Asn Gly Tyr Ile Met Asp Thr Leu Pro Gly Leu Val Met
1025                1030                1035                1040
Ala Gln Asp Gln Arg Ile Arg Trp Tyr Leu Leu Ser Met Gly Ser Asn
                1045                1050                1055
Glu Asn Ile His Ser Ile His Phe Ser Gly His Val Phe Thr Val Arg
                1060                1065                1070
Lys Lys Glu Glu Tyr Lys Met Ala Leu Tyr Asn Leu Tyr Pro Gly Val
            1075                1080                1085
Phe Glu Thr Val Glu Met Leu Pro Ser Lys Ala Gly Ile Trp Arg Val
        1090                1095                1100
```

```
Glu Cys Leu Ile Gly Glu His Leu His Ala Gly Met Ser Thr Leu Phe
1105                1110                1115                1120

Leu Val Tyr Ser Asn Lys Cys Gln Thr Pro Leu Gly Met Ala Ser Gly
            1125                1130                1135

His Ile Arg Asp Phe Gln Ile Thr Ala Ser Gly Gln Tyr Gly Gln Trp
        1140                1145                1150

Ala Pro Lys Leu Ala Arg Leu His Tyr Ser Gly Ser Ile Asn Ala Trp
    1155                1160                1165

Ser Thr Lys Glu Pro Phe Ser Trp Ile Lys Val Asp Leu Leu Ala Pro
1170                1175                1180

Met Ile Ile His Gly Ile Lys Thr Gln Gly Ala Arg Gln Lys Phe Ser
1185                1190                1195                1200

Ser Leu Tyr Ile Ser Gln Phe Ile Ile Met Tyr Ser Leu Asp Gly Lys
            1205                1210                1215

Lys Trp Gln Thr Tyr Arg Gly Asn Ser Thr Gly Thr Leu Met Val Phe
        1220                1225                1230

Phe Gly Asn Val Asp Ser Ser Gly Ile Lys His Asn Ile Phe Asn Pro
    1235                1240                1245

Pro Ile Ile Ala Arg Tyr Ile Arg Leu His Pro Thr His Tyr Ser Ile
1250                1255                1260

Arg Ser Thr Leu Arg Met Glu Leu Met Gly Cys Asp Leu Asn Ser Cys
1265                1270                1275                1280

Ser Met Pro Leu Gly Met Glu Ser Lys Ala Ile Ser Asp Ala Gln Ile
            1285                1290                1295

Thr Ala Ser Ser Tyr Phe Thr Asn Met Phe Ala Thr Trp Ser Pro Ser
        1300                1305                1310

Lys Ala Arg Leu His Leu Gln Gly Arg Ser Asn Ala Trp Arg Pro Gln
    1315                1320                1325

Val Asn Asn Pro Lys Glu Trp Leu Gln Val Asp Phe Gln Lys Thr Met
    1330                1335                1340

Lys Val Thr Gly Val Thr Thr Gln Gly Val Lys Ser Leu Leu Thr Ser
1345                1350                1355                1360

Met Tyr Val Lys Glu Phe Leu Ile Ser Ser Ser Gln Asp Gly His Gln
            1365                1370                1375

Trp Thr Leu Phe Phe Gln Asn Gly Lys Val Lys Val Phe Gln Gly Asn
        1380                1385                1390

Gln Asp Ser Phe Thr Pro Val Val Asn Ser Leu Asp Pro Pro Leu Leu
    1395                1400                1405

Thr Arg Tyr Leu Arg Ile His Pro Gln Ser Trp Val His Gln Ile Ala
    1410                1415                1420

Leu Arg Met Glu Val Leu Gly Cys Glu Ala Gln Asp Leu Tyr
1425                1430                1435

<210> SEQ ID NO 2
<211> LENGTH: 402
<212> TYPE: DNA
<213> ORGANISM: Artificial Sequence
<220> FEATURE:
<223> OTHER INFORMATION: Description of Artificial Sequence:Derived from
      Epstein-Barr virus sequence

<400> SEQUENCE: 2
ggcaatggag cgtgacgaag ggccccaggg ctgaccccgg caaacgtgac ccggggctcc      60
ggggtgaccc aggcaagcgt ggccaagggg cccgtgggtg acacaggcaa ccctgacaaa    120
```

-continued

```
ggcccccag  gaaagacccc  cgggggcat   cggggggtg   ttggcgggtc  atggggggg    180 cgggtcatgc  cgcgcattcc  tggaaaaagt  ggaggggcg   tggccttccc  cccgcggccc  240
cctagccccc  ccgcagagag  cggcgcaacg  gcgggcgagc  ggcgggggt   cgggtccgc   300 gggctccggg  ggctgcggc   ggtggatggc  ggctggcgtt  ccggggatcg  ggggggggtc  360 gggggcgct   gcgcgggcgc  agccatgcgt  gaccgtgatg  ag                       402
```